United States Patent [19]

Jackson et al.

[11] Patent Number: 4,635,790
[45] Date of Patent: Jan. 13, 1987

[54] CONTAINER PACKAGE FOR STAINING A BIOLOGICAL SPECIMEN

[75] Inventors: Frank W. Jackson, Mechanicsburg; David Schlossberg, Merion, both of Pa.

[73] Assignee: Bio-Innovations, Camp Hill, Pa.

[21] Appl. No.: 699,993

[22] Filed: Feb. 8, 1985

Related U.S. Application Data

[63] Continuation-in-part of Ser. No. 372,591, Apr. 28, 1982, abandoned.

[51] Int. Cl.$^4$ .................. B05C 3/00; B05C 19/02; B65D 81/24; B65D 85/48
[52] U.S. Cl. .................. 206/210; 206/456; 118/429; 118/428; 424/3
[58] Field of Search .............. 53/431; 118/428, 429; 206/205, 209, 210, 456; 424/3; 427/2, 4, 430.1

[56] References Cited

U.S. PATENT DOCUMENTS

| | | | |
|---|---|---|---|
| 2,664,358 | 12/1953 | Eichler | 206/205 |
| 2,714,443 | 8/1955 | Kuvin | 206/205 |
| 2,998,127 | 8/1961 | Stewart | 206/456 |
| 3,398,825 | 8/1968 | Flook et al. | 206/209 |
| 3,880,278 | 4/1975 | Brown | 206/205 |
| 4,240,547 | 12/1980 | Taylor | 206/456 |

Primary Examiner—Michael R. Lusignan
Attorney, Agent, or Firm—Eugene Chovanes

[57] ABSTRACT

A disposable container package for staining a biological specimen affixed to the face of a microscopic slide comprises a body member having a generally rectangular upwardly-opening cavity for receiving a slide. The cavity has a height less than the length of the slide and a cross-sectional area less than or equal to twice the cross-sectional area of the slide and is of a size sufficient to receive only a single slide. Guide slots are arranged in the cavity for maintaining a spaced relationship between the opposed faces of the slide and the cavity walls. A quantity of staining liquid partially fills the cavity, the depth of which prior to the insertion of the slide in the cavity is less than the distance between the upper edge of the specimen and the inserted end of the slide, and the depth of which when the slide is fully inserted in the cavity is sufficient to cover the specimen with a thin film of staining liquid. A removable seal closes the cavity prior to use of the container.

16 Claims, 16 Drawing Figures

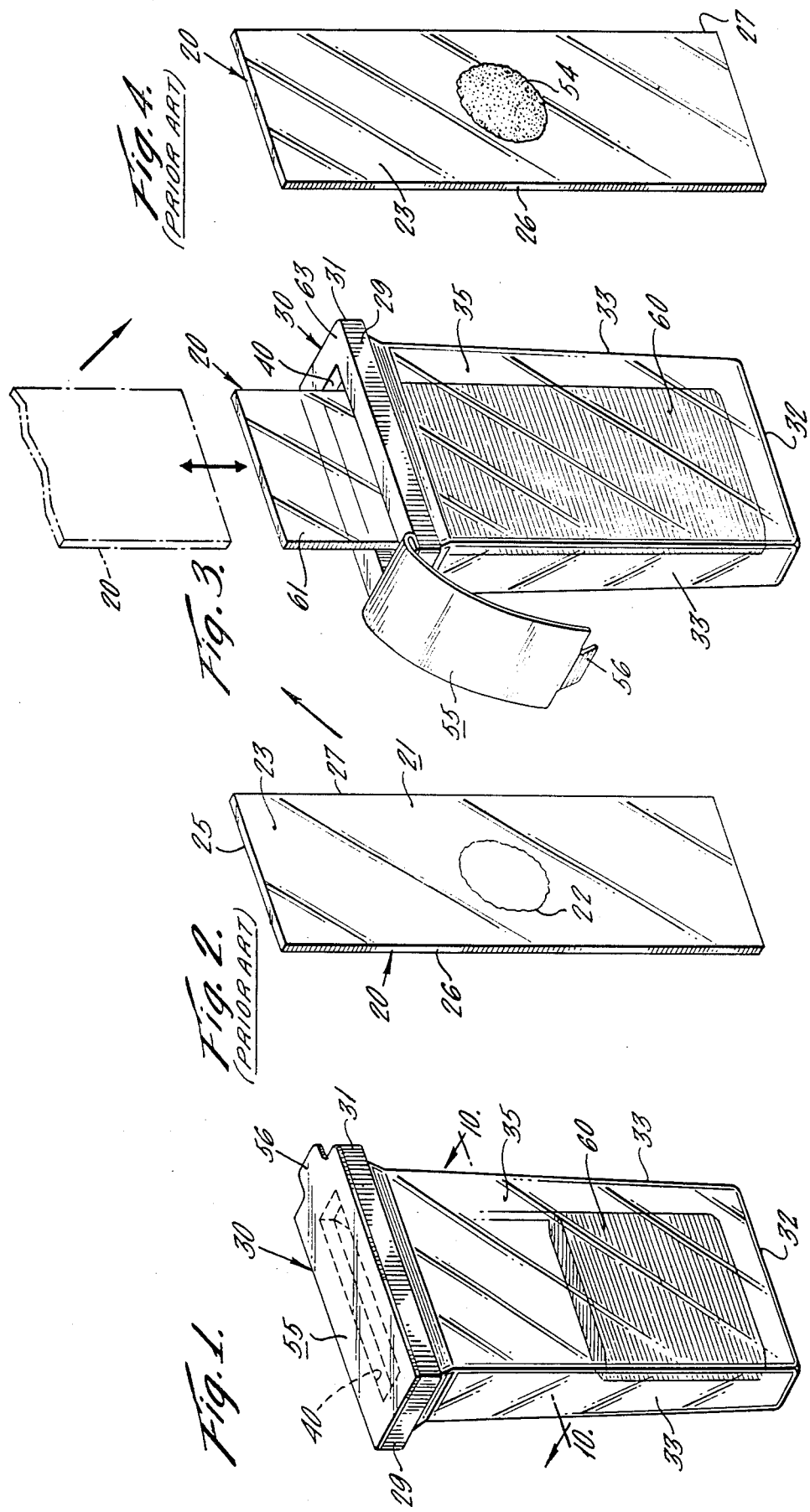

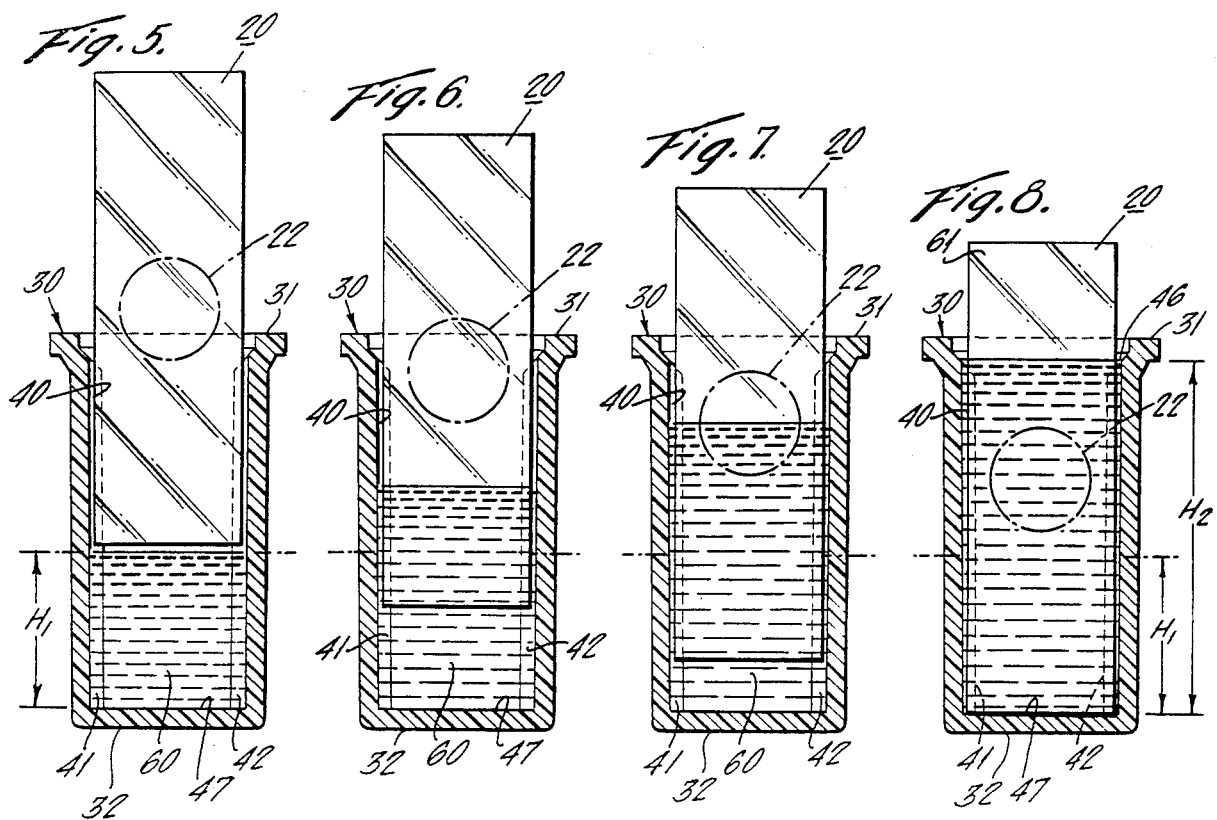
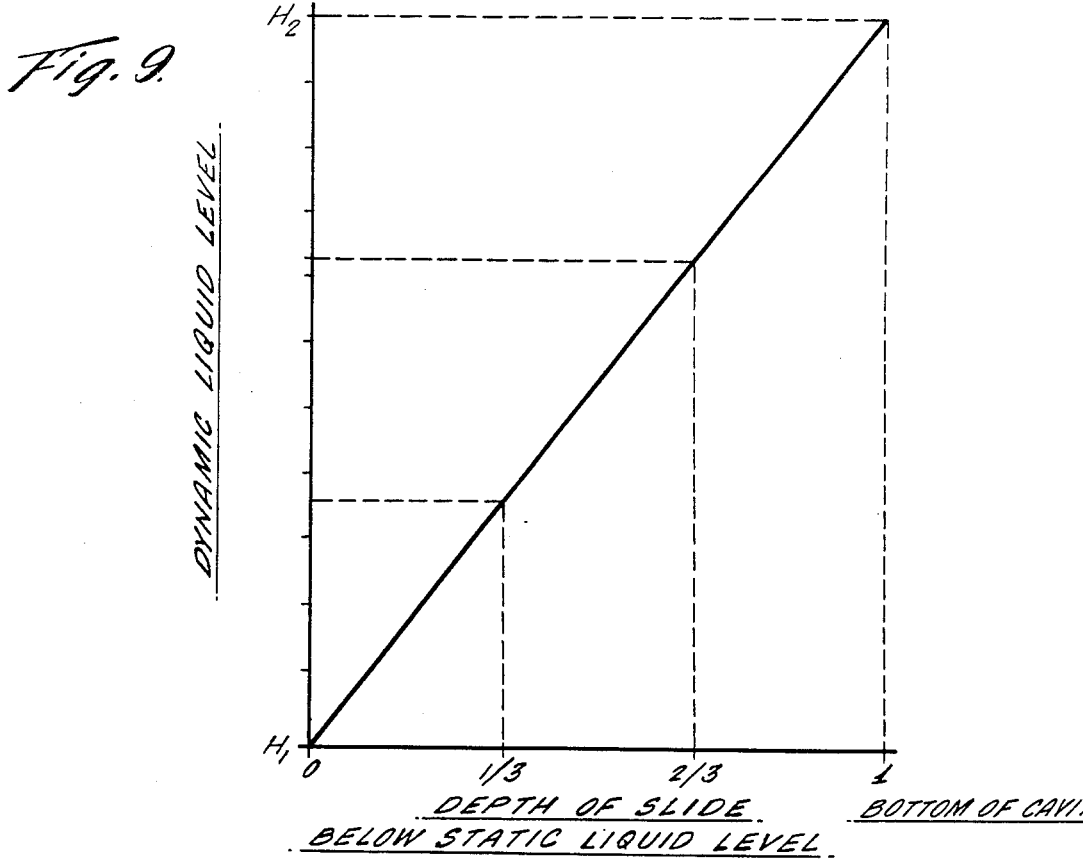

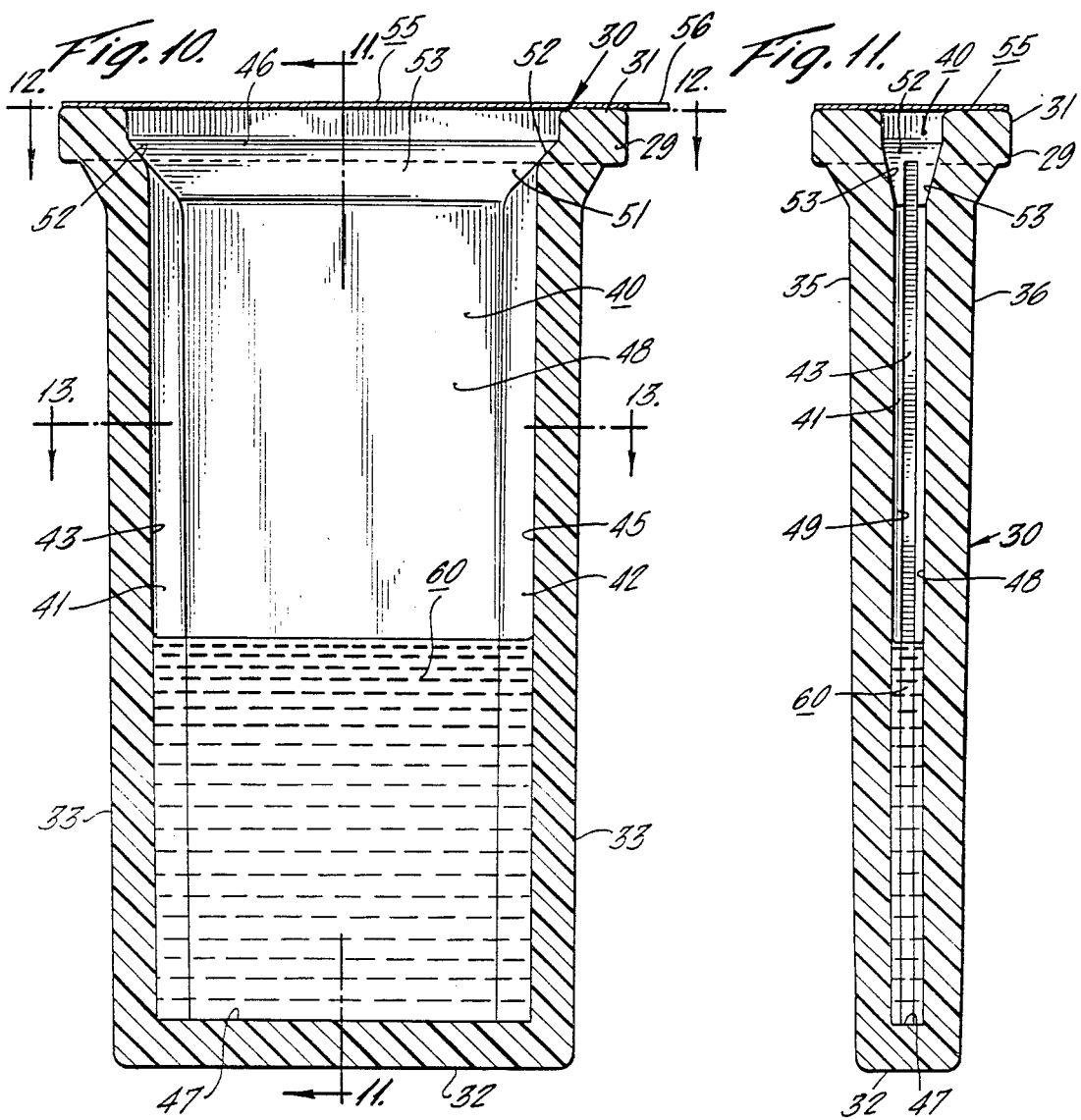

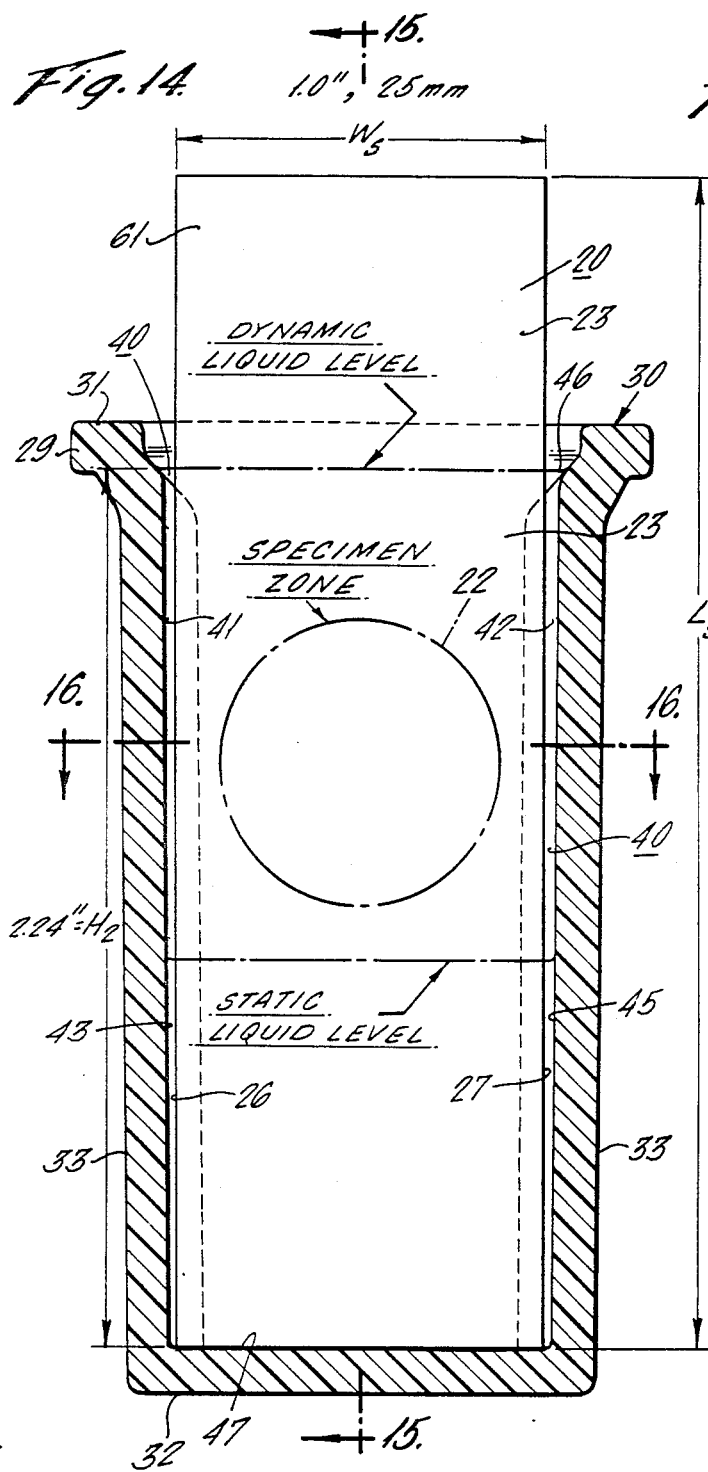
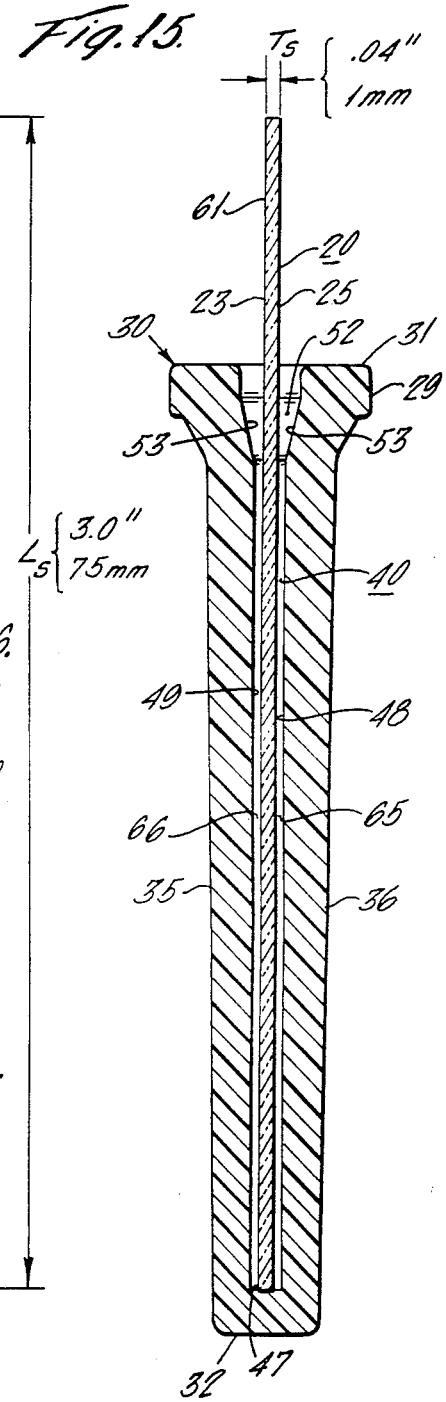
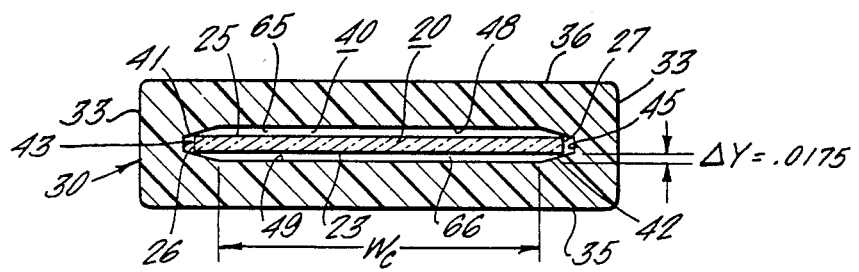

CONTAINER PACKAGE FOR STAINING A BIOLOGICAL SPECIMEN

FIELD OF INVENTION

This application is a continuation-in-part of Ser. No. 372,591 filed Apr. 28, 1982, now abandoned.

The invention generally relates to an apparatus for the microscopic examination of biologic specimens mounted on glass slides, and specifically relates to a container package for the staining of such biologic specimens in preparation for microscopic examination. The staining and examining of biologic specimens occurs daily in great numbers in hospital laboratories, emergency rooms, clinics, biology departments, blood banks, and many physicians' offices, veterinarian offices and hospitals. The slides used are of glass and generally have a 1"×3" face dimension and a 1 mm thickness. Some slides may have a slightly different face dimension of 25 mm×75 mm or a different thickness of 1.2 mm. The specimens to be stained and examined may, for instance, be tissue, blood, sputum, or urine. The biologic specimens are usually smeared on the glass slide and left to air dry, often with heat or reagent fixation.

BACKGROUND OF THE INVENTION

To stain a biologic specimen fixed on a glass slide, it is necessary to bring a staining liquid or reagent into contact with the specimen on the slide.

One means for staining a specimen affixed to a slide is disclosed by the Scharf U.S. Pat. No. 3,132,744 and comprises a disposable package for receiving two slides to be stained. The package is filled with a staining liquid prior to use, and the slides are immersed in the pool of liquid in order to stain the specimens. While the package disclosed by Scharf allows for on site staining of microscopic slides, several disadvantages are also involved. A relatively large quantity of expensive staining liquid is used for the immersion and staining of the two slides, much more than is necessary for the actual staining of the specimens. Moreover, the centrally extending ribs which separate the two slides can disturb a specimen affixed to the face of a slide.

In another known and widely used apparatus for staining slides, the slide is placed horizontally, specimen up, on a rack suspended in a sink. The staining liquid is poured or dripped from a bottle over the slide to flood the specimen. This apparatus also wastes expensive staining liquid, since much more liquid is generally squeezed or dripped than is actually needed for staining. Also, the sink becomes stained and unsightly after a period of time from the overflow liquid. The operator's fingers become stained when the specimen is picked up. When the bottle reagents remain in the sink area for a prolonged period of time, the fluid can deteriorate or become contaminated. It generally requires from 6 cc to 8 cc of each reagent to perform a specific examination using the above technique.

A less known apparatus comprises a rack in which the slide or slides are vertically placed, and the rack with the slide therein is dipped into a container of staining liquid. This too uses an amount of dye far in excess of that actually necessary for staining, and, where the reagent is used for more than one slide, contamination often occurs. Likewise, this technique involves pouring liquid from bottles into containers and pouring the staining liquid from containers into sinks.

Another less common means is an automated staining device. Large hospitals with heavy workloads are more inclined to use this type of apparatus. The machinery involved in such an automated device is extremely expensive and can only be justified where the amount of staining is extremely heavy. The cost of such machines prohibits their use in most staining operations. Furthermore, automated staining devices are only available for one or two stains.

SUMMARY OF THE INVENTION

The present invention comprises a container package for staining biological specimens. The container package includes a body member having an upwardly-opening cavity or chamber therein for receiving a microscopic slide having a specimen on one face. The chamber has a cross-sectional area less than or equal to twice the cross-sectional area of the slide and has a height less than the length of the slide. A quantity of staining liquid partially fills the chamber. The depth of the liquid prior to the insertion of the slide in the chamber is less than the distance between the upper edge of the specimen and the inserted end of the slide. The amount of liquid may be as small as 1 to 2 cc. When the slide is fully inserted in the container package the staining liquid is displaced so as to form only a thin film of staining liquid on each face of the slide. A removable seal closes the upper opening prior to use of the container.

When the stained slide is vertically withdrawn from the chamber, the staining liquid drains off the slide and remains in the chamber. The container and used liquid may then be reused or disposed of. The slide is inserted and withdrawn from the chamber by the portion of the slide which continuously extends above the chamber.

In the present invention, substantially less liquid is required in the container than used in the devices of the prior art; a fresh batch of reagent may be provided for each specimen; sinks are not stained since the liquid remains within the container; the operators' fingers do not become stained since the staining liquid remains within the chamber; and use of the present container is quicker and more time efficient.

The container is a disposable one and is generally intended for one use, although the container may be reused if desired. A cover, seal or stopper seals the chamber and liquid until the container is used. The seal or cover may be made tamper-resistant if desired.

BRIEF DESCRIPTION OF THE DRAWING

FIG. 1 is a perspective view of the container package of the present invention;

FIG. 2 is a perspective view of a conventional glass slide of either metric or English dimensions;

FIG. 3 is a perspective view similar to FIG. 1 disclosing the container package with the cover removed and a slide inserted;

FIG. 4 is a view of a conventional slide such as disclosed in FIG. 2, having been stained in the container package of the present invention;

FIGS. 5 through 8 are sequentially sectional elevational views disclosing a slide being inserted into the container package of the present invention;

FIG. 9 is a graph illustrating a principle shown in FIGS. 5 through 8;

FIG. 10 is an enlarged sectional elevational view taken on the line 10—10 of FIG. 1, disclosing in greater detail the interior design of the staining container package of FIG. 1;

FIG. 11 is a transverse sectional view taken on the line 11—11 of FIG. 10, disclosing further details of the container;

FIG. 12 is a plan view of the staining container package directly beneath the foil cover taken on the line 12—12 of FIG. 10, disclosing details of the slide entrance aperture on the upper face of the staining container;

FIG. 13 is a sectional plan view taken on the line 13—13 of FIG. 10, disclosing the profile and proportions of the interior chamber and slide-guiding slots of the staining container package;

FIG. 14 is an enlarged sectional elevational view disclosing a slide fully inserted in the staining container package, such as is shown in FIG. 3, and disclosing the combined proportions and the positions of the slide and slide-staining container package in use;

FIG. 15 is a transverse sectional elevational view taken on the line 15—15 of FIG. 14 disclosing central positioning of a slide carried in slots and liquid displacement areas formed on the front and rear face of the inserted slide in the container package; and FIG. 16 is a sectional plan view taken on the line 16—16 of FIG. 14, disclosing relative proportions and positions of the slide and the slide-staining container package, and liquid displacement areas formed on the front and rear side of the slide.

DETAILED DESCRIPTION OF THE INVENTION

The container package of the present invention is adapted for use with a conventional slide 20 as seen particularly in FIGS. 2 and 4. The slide 20 is simply a rectangular piece of glass 21 on which a specimen 22 is mounted for microscopic examination. This slide has opposed flat surfaces or faces 23 and 25, opposed long edges 26 and 27, and opposed short edges.

The most commonly used slide has a length ($L_S$) of approximately 3", a width ($W_S$) of approximately 1", and a thickness ($T_S$) of approximately 1 mm. In some instances, the slide may have a $L_S$ of 75 mm and $W_S$ of 25 mm, or a $T_S$ of 1.2 mm.

These dimensions may vary slightly with different manufacturers. For instance, thicknesses may vary from 0.0525" to 0.0325", and the width may vary from 1.016" to 0.964".

The specimen 22 is prepared and then affixed to a face of the slide in any well known manner such as by use of air drying, heat, or reagent fixation. The specimen 22 is generally positioned at the center of one of the slide faces, with a clear zone, free of the specimen, on each end of the face. The specimen is virtually invisible at this point, prior to staining.

The slide 20, with the unstained specimen 22 thereon, is intended to be inserted into a container package having a container or body member 30. Container 30 is desirably formed of a transparent or translucent plastic into a generally long rectangular configuration having proportions generally conforming to the proportion of the slide 20. The container is intended to be used in a vertical position, with its longitudinal axis extending vertically, and has a top 31, a bottom 32, edges 33 and sides 35 and 36. A collar or flange 29 surrounds top 30 and has a flat surface thereon.

An internal cavity or chamber 40, likewise is rectangular in configuration and similarly conforms generally to the proportions of the slide 20 and is of a size sufficient to receive a single slide. The internal cavity 40 has opposed tapered vertical tracks 41 and 42, along the vertical edges 43 and 45 of the cavity. The tracks 41 and 42 extend from the top 46 of the cavity to the bottom 47. The cavity also has opposed sides 48 and 50.

The cavity 40 has at its upper end a sloping, downwardly converging portion 51 having beveled edges 52 and sides 53.

A cover or seal 55 is affixed to the top 31 on the collar or flange 29 by suitable means, such as heat sealing or adhesive. The cover is intended to be peeled back by grasping and pulling on tab 56 prior to use, so that the cavity 40 is exposed. The cover may in this manner be made tamper-resistant.

A quantity of staining liquid 60 is contained within the cavity and extends about halfway up the cavity, as seen in FIGS. 1 and 10. The depth of the liquid prior to the insertion of a slide in the cavity is less than the distance between the upper edge of the specimen zone and the inserted end of the slide.

The container package of the present invention is intended to be manufactured at a central facility whereat it is sealed with the staining liquid therein, as seen in FIG. 1.

As seen in FIGS. 5 through 8, there are disclosed in sequence views of a slide 20 being inserted into the cavity 40. In FIG. 5, the slide 40 with a biological specimen 22 to be stained affixed thereon, is shown entering the cavity 40 guided on tacks or slots 41 and 42. The faces 23 and 25 of slide 20 are spaced from the opposing slides 49 and 48, respectively, as seen best in FIGS. 15 and 16 by means of the guide tracks. The slide in FIG. 5 is just about to contact the upper surface of the quantity of liquid 60. The level of liquid 60 prior to insertion of the slide is the static liquid level. The static liquid level is at a height of $H_1$ above the bottom of the cavity.

In FIGS. 6 and 7, the slide progressively descends into the cavity below the liquid level, and the level of the liquid is displaced and rises until the dynamic fluid level reaches $H_2$ as seen in FIG. 8, when the slide is fully inserted. At this point, the staining liquid entirely covers specimen 22. Preferably $H_1$ is approximately one-half of $H_2$. $H_2$ also represents the height of the cavity as seen best in FIG. 14.

In FIG. 9, the principle described and shown in FIGS. 5 through 8, is illustrated in graph form. As the slide is submerged below the static liquid level, there is a corresponding rise in the dynamic liquid level of the staining liquid in virtually a straight line relationship.

As the slide is removed from the staining liquid, after being left therein for an adequate period to accomplish staining, the slide is withdrawn and the reverse sequence occurs. The liquid level falls correspondingly as the liquid drains from the sides of the slide into the cavity. There is some residual staining liquid that adheres to the specimen and the slide, and of course the liquid height at the end of the staining drops correspondingly below the static liquid level when the slide is withdrawn from the container. The slide when withdrawn from the container 30 has thereon the stained specimen 54 as seen in FIG. 4. Since the container is generally intended for a one-time use, such a drop in the liquid height and volume is not objectionable.

The converging or tapered guide portion 51 having beveled edges 52 and beveled side 53 as disclosed in FIG. 10 permits easy insertion of the slide into the guide tracks 41 and 42. It also acts as a well to catch any overflow of the staining liquid, including any splashing where the slide is dropped rapidly into the cavity. The collar or guide flange portion 29 extends around the upper end or top of the container and is integral therewith. Preferably, flange 29 includes a flat top portion 63 which permits a foil or other type of cover 55 to be suitably secured thereto as by adhesive, or by a suitable heat-sealing technique. The foil can be of a metallic or a plastic material capable of being peeled back from the container by grasping a tab portion 56 and pulling to a completely open position, as seen in FIG. 3. The cover in the sealing and covering position is disclosed in FIGS. 10 and 11. The cover may in this manner be secured such that the container is rendered tamper-resistant.

There is variability in the width and thickness of slides, even those claiming to have specific dimensions. By tapering the tracks, the container will receive a slide of variable thickness and variable width and still keep the slide away from the inside wall of the cavity. Additionally, the tapered tracks assure that only the edge of the slide will touch the track and not the surface which contains the specimen. Thus, the specimen is not disturbed by the guide means.

The slide 20 when inserted into the cavity 40 on the tracks 41 and 42 assumes a very definite position and posture within the cavity and with respect to the sides or walls 48 and 49 of the cavity 40.

As seen in FIGS. 14 and 16 inclusive, the slide 20 when fully inserted into the container in the bottom-most position has a top portion 61 which extends above the cavity 40 and top 31 of the container 30. Thus, the height of the cavity 40 is less than the length of the slide to be inserted therein. The top portion 61 of the slide 20 is clear of any specimen 22, since the specimen zone is completely disposed within the cavity when the slide is inserted therein. The specimen zone is conventionally in the middle of the slide as shown in FIG. 14 by phantom lines. The portion 61 of the slide 20 remaining above the device 30 is used to grasp the slide for inserting into the container and for withdrawing the slide from the container. The slide is also grasped by this portion during the rinsing of the slide subsequent to the staining. In this way, the operator's fingers remain free of contact with the staining solution and free of the dye. Preferably, approximately one-sixth of the length of the slide $L_S$ extends above the device 30.

The specimen 22 is stained when the slide is fully inserted as disclosed particularly in FIGS. 14 through 16 inclusive. The slide as seen particularly in FIGS. 15 and 16 is positioned centrally of the cavity 40 and spaced from walls or sides 48 and 49. The slide 20 has adjacent to each face thereof spaces 65 and 66 which each contain a thin film of staining liquid. The slide can be inserted with the specimen 22 facing in either direction as the slide 20 enters the cavity. The face of the slide 20 with the specimen 22 thereon is positioned so that the specimen 22 cannot contact the sides of the cavity, but rather the slide is held by the tracks 41 and 42 in a way that exposes the specimen to the staining liquid in the space 65 or 66 formed by the slide and the side of the cavity. A minimum amount of staining liquid in the form of a thin film is presented to stain the specimen when the slide is so positioned. This is clearly shown in the sectional views in FIGS. 15 and 16.

It will be seen from the above description that the space 65 and 66 adjacent to each face of the slide when the slide is fully inserted into the cavity is a flat thin space which contains a suitable amount, i.e. a thin film, of staining liquid to properly stain the specimen thereon, without excess use of such liquid. Furthermore, the slide itself is used to position this liquid adjacent to the faces of the slide, and the specimen on one of the faces. It will be seen that it does not matter as to which direction the specimen faces when inserted into the cavity, since there is a thin film of staining liquid on both faces of the slide.

The slide itself, in cooperation with the container, creates the thin film adjacent to the slide faces for staining, and then permits the liquid in those spaces to drain back into the bottom of the cavity when the slide is removed.

In FIGS. 10 through 16 inclusive, there is shown in detail the interior of the container of FIG. 1. $W_S$ is the width of the slide 20, $L_S$ is its length, and $T_S$ is its thickness. $H_2$, which is the height of the cavity, as well as the height of the dynamic liquid level discussed above, is approximately three-quarters of the slide length, $L_S$.

The tracks 41 and 42 comprise tapered walls in the edges of the cavity, as shown. The width between the tracks, $W_T$, as seen in FIG. 13, is slightly greater, for instance, 0.02" greater, than the width of the slide $W_S$, so that there is adequate clearance for the slide to move in the tracks. $T_T$, the thickness of the track at its tapered end, is slightly less, for instance, 0.016" less, than the thickness of the slide, $T_S$. Y, the thickness or cross-sectional area of the cavity is approximately twice the slide thickness, $T_S$. By virtue of the tapered tracks 41 and 42, the slide, when inserted in the tracks, is centrally spaced between the sidewalls of the cavity, 48 and 49. Where the thickness of the cavity is twice that of the slide, the thickness of the spaces formed on each face of the slide when the slide is inserted will be approximately one-half the thickness of the slide. Preferably, the thickness or cross-sectional area of the cavity is less than or equal to twice the thickness of the slide.

By virtue of the tapered tracks 41 and 42, slides with slightly varying dimensions as set forth above, will be suitably spaced within cavity 40. The tapered walls of the tracks 41 and 42 will compensate for these slight variations by guiding the slide at its edges while still positioning the slide in the cavity of the container. Even with a slide having the smallest width and/or thickness within the variable dimensions, the slide faces are still spaced from the sides of the cavity, although edges of the slide may not be in firm contact with the tracks. Even though such a relatively small slide may have more freedom to move about within the cavity than a relatively large slide, the restraint imposed on the corners of the slide by the tapered walls of the tracks keeps the slide spaced from the cavity walls so that a film of staining fluid can be formed adjacent the slide faces.

It should be understood that the slide dimensions given above are merely illustrative to indicate a suitably dimensioned container to practice the invention.

In view of our invention and disclosure, variations and modifications to meet individual whim or particular need will doubtless become evident to others skilled in the art to obtain all or part of the benefits of our invention without copying the structure shown, and we therefore claim all such insofar as they fall within the reasonable spirit and scope of our claims.

What is claimed is:

1. A disposable container package for applying a staining liquid to a specimen affixed to a specimen zone centrally arranged on one of the opposed faces of a glass slide, said container package comprising:

(a) a generally rectangular body member arranged with its longitudinal axis extending vertically and containing a generally rectangular upwardly-opening cavity for receiving the slide, the cavity having such a height less than the length of the slide as to cause one end of the slide to extend above said body member and the specimen zone to be completely disposed within the cavity when the slide is fully inserted in the cavity, said cavity having a horizontal cross-sectional area no greater than twice the cross-sectional area of the slide and being of a size sufficient to receive only a single slide;

(b) guide means arranged in the cavity for maintaining a spaced relationship between the opposed faces of the inserted slide and the cavity walls;

(c) a quantity of staining liquid partially filling the cavity, the depth of said staining liquid prior to insertion of the slide in the cavity being less than the distance between the upper edge of the specimen zone and the inserted end of the slide, the quantity of said staining liquid being sufficient to raise the level of said liquid when the slide is fully inserted in the cavity to a level sufficient to cover the specimen zone on the slide with a thin film of said staining liquid, thereby staining the specimen affixed thereto; and (d) a removable seal closing the upward end of the cavity, thereby to contain said staining liquid prior to the use of said container package.

2. A container package as defined by claim 1, wherein said guide means engage the side edges of the inserted slide.

3. A container package as defined by claim 1, wherein the inserted end of the fully inserted slide bottoms on the lower end of the cavity.

4. A container package as defined by claim 1, wherein the width of the cavity is slightly greater than the width of the slide and the thickness of the cavity is less than twice the thickness of the slide.

5. A container package as defined by claim 1, wherein said staining liquid substantially fills the cavity when the slide is fully inserted therein.

6. A container package as defined by claim 1, wherein the depth of said staining liquid following insertion of the slide is substantially twice the depth of said staining liquid prior to insertion of the slide.

7. A container package as defined by claim 1, wherein the quantity of said staining liquid in the cavity comprises less than 2 cc.

8. A container package as defined by claim 1, wherein said removable seal is affixed by heat sealing.

9. A container package as defined by claim 1, wherein the depth of said staining liquid prior to insertion of the slide is approximately one half the height of the cavity and the depth of said staining liquid following insertion of the slide is approximately the height of the cavity.

10. A container package as defined by claim 1, wherein said body member comprises a transparent plastic material.

11. A disposable container package for applying a staining liquid to a specimen affixed to a specimen zone on one of the opposed faces of a glass slide, the specimen zone being centrally disposed between the slide ends, said container package comprising:

a body member having an upwardly-opening cavity therein for receiving the slide, a quantity of staining liquid partially filling said cavity, and a removable seal closing said cavity to contain said liquid prior to use of said container package, said cavity having a height shorter than the length of the slide to permit an end of the slide to extend above said container when the slide is fully inserted in the cavity, the specimen zone being disposed completely within the cavity when the slide is fully inserted into the cavity regardless of which end of the slide is so inserted, means for maintaining a spaced relationship of the opposed faces of the specimen zone of the slide and the cavity walls, said cavity being of a size sufficient to receive only a single slide and having a cross-sectional area no greater than twice the cross-sectional area of the slide, the depth of the staining liquid prior to insertion of the slide being less than the distance between the upper edge of the specimen zone and the inserted end of the slide, the insertion of the slide displacing said liquid and raising the liquid level to a level sufficient to cover the specimen zone and thereby stain the specimen fixed thereto when a slide is so positioned between the cavity walls.

12. A container package for applying a staining liquid to a specimen affixed to a specimen zone centrally arranged on one of the opposed faces of a glass slide, said container package comprising:

(a) a generally rectangular body member arranged wtih its longitudinal axis extending vertically and including a flange portion at its upper end and contianing a generally rectangular upwardly-opening slot-like cavity therein for receiving the slide, the cavity having such a height less than the length of the slide as to permit one end of the slide to extend above said body member and the specimen zone to be completely disposed within the cavity when the slide is fully in the cavity, said cavity having a width slightly greater than the width of the slide and having a cross-sectional thickness less than twice the thickness of the slide, the bottom wall of the cavity engaging the end of a fully inserted slide;

(b) guide means arranged in the cavity for engaging the side edges of the slide and preventing contact of the opposed faces of the slide with the cavity walls;

(c) a quantity of staining liquid partially filling the cavity, the depth of said staining liquid prior to insertion of the slide in the cavity being less than the distance between the upper edge of the specimen zone and the inserted end of the slide, the quantity of said staining liquid being sufficient to raise the level of said liquid when the slide is fully inserted in the cavity to a level sufficient to cover the specimen zone on the slide with a thin film of said staining liquid, thereby staining the specimen affixed thereto; and (d) a removable seal adhered to said flange portion of said body member and closing the upward end of the cavity to contain said staining liquid prior to the use of said container package.

13. A container package as defined by claim 12, wherein said staining liquid substantially fills the cavity when the slide is fully inserted therein.

14. A container package as defined by claim 12, wherein the depth of said staining liquid following insertion of the slide in the cavity is substantially twice the depth of said staining liquid prior to insertion of the slide.

15. A container package as defined by claim 12, wherein the quantity of said staining liquid in the cavity comprises less than 2 cc.

16. A container package for applying a staining liquid to a specimen affixed to a specimen zone on one of the opposed faces of a glass slide, the specimen zone being generally centrally disposed equidistant the slide ends, said container package comprising a body member having an upwardly-opening slot-like cavity therein for receiving the slide, a quantity of staining liquid partially filling said cavity, and a removable seal closing said cavity to contain said liquid prior to use of said container package, the cavity having a rectangular vertical section shape, the width of the cavity being slightly greater than the width of the slide and the thickness of the cavity being less than twice the thickness of the slide, the cavity having a height shorter than the length of the slide to permit an end of the slide to extend above said container when the slide is fully inserted in the cavity, the slide when fully inserted engaging the bottom of the cavity, the specimen zone being disposed completely within the cavity when the slide is fully inserted into the container package regardless of which end of the slide is so inserted, the configuration of the cavity permitting engagement of the side edges of the slide with the cavity walls and preventing contact of the specimen zone of the opposed faces of the glass slide with the cavity walls, the depth of the staining liquid prior to insertion of the slide being less than the distance between the upper edge of the specimen zone and the inserted end of the slide, the insertion of the slide displacing said liquid and raising the liquid level to a level sufficient to cover the specimen zone and thereby stain the specimen fixed thereto when the slide is positioned between the cavity walls.

* * * * *